United States Patent
Matsumoto et al.

(10) Patent No.: US 8,783,111 B2
(45) Date of Patent: Jul. 22, 2014

(54) ULTRASONIC TESTING PROBE AND ULTRASONIC TESTING APPARATUS

(75) Inventors: Hirotoshi Matsumoto, Tokyo (JP);
Masatsugu Shimizu, Tokyo (JP);
Kiyotaka Aoki, Tokyo (JP); Shinichi Tsuji, Kitakyushu (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 215 days.

(21) Appl. No.: 13/386,799

(22) PCT Filed: Aug. 12, 2010

(86) PCT No.: PCT/JP2010/063691
§ 371 (c)(1),
(2), (4) Date: Jan. 24, 2012

(87) PCT Pub. No.: WO2011/021564
PCT Pub. Date: Feb. 24, 2011

(65) Prior Publication Data
US 2012/0118064 A1    May 17, 2012

(30) Foreign Application Priority Data
Aug. 21, 2009 (JP) .................................. 2009-191794

(51) Int. Cl.
*G01N 29/00* (2006.01)
(52) U.S. Cl.
USPC .................................. 73/632; 73/599; 73/622
(58) Field of Classification Search
USPC ............ 73/632, 596, 599, 600, 602, 627, 628
See application file for complete search history.

(56) References Cited

U.S. PATENT DOCUMENTS

| | | | | |
|---|---|---|---|---|
| 4,137,779 A | * | 2/1979 | Wustenberg et al. | ............ 73/627 |
| 4,398,421 A | * | 8/1983 | White | ............................. 73/597 |

(Continued)

FOREIGN PATENT DOCUMENTS

| | | |
|---|---|---|
| CN | 2497312 | 6/2002 |
| JP | 58-53756 | 3/1983 |

(Continued)

OTHER PUBLICATIONS

International Search Report issued Sep. 21, 2010 in corresponding International Application No. PCT/JP2010/063691.

(Continued)

*Primary Examiner* — J M Saint Surin
(74) *Attorney, Agent, or Firm* — Wenderoth, Lind & Ponack, L.L.P.

(57) ABSTRACT

Provided are an ultrasonic testing probe and an ultrasonic testing apparatus capable of reducing the time required for flaw detection while maintaining the flaw-detection capability, irrespective of the shape of the inner surface of a tested object. A first probe (21) and a second probe (22) are provided, in each of which a plurality of oscillators that transmit ultrasonic waves to a tested object (T) and detect the ultrasonic waves reflected from the tested object (T) are arrayed. The first probe (21) is disposed closer to a flaw in the tested object (T) than the second probe (22) is. The first probe (21) generates longitudinal ultrasonic waves that propagate on an inner surface (T5) of the tested object (T) opposite to an outer surface (T2) thereof where the first probe (21) and the second probe (22) are disposed and transverse ultrasonic waves that propagate from the outer surface (T2) toward an inside of the tested object (T). The second probe (22) generates longitudinal ultrasonic waves that propagate on the outer surface (T2) and longitudinal ultrasonic waves that propagate from the outer surface (T2) toward the inside of the tested object (T).

2 Claims, 5 Drawing Sheets

(56) References Cited

U.S. PATENT DOCUMENTS

| | | | |
|---|---|---|---|
| 4,570,487 A * | 2/1986 | Gruber | 73/624 |
| 4,658,649 A | 4/1987 | Brook | |
| 6,405,596 B1 | 6/2002 | Kruzic | |
| 6,640,632 B1 * | 11/2003 | Hatanaka et al. | 73/598 |
| 7,900,516 B2 * | 3/2011 | Fukutomi et al. | 73/598 |
| 8,051,717 B2 * | 11/2011 | Fukutomi et al. | 73/598 |
| 2005/0183505 A1 | 8/2005 | Kono et al. | |
| 2006/0116582 A1 * | 6/2006 | Yoshida et al. | 600/458 |
| 2011/0230750 A1 * | 9/2011 | Tateyama | 600/407 |

FOREIGN PATENT DOCUMENTS

| | | |
|---|---|---|
| JP | 61-283864 | 12/1986 |
| JP | 63-63763 | 4/1988 |
| JP | 64-59152 | 3/1989 |
| JP | 7-128304 | 5/1995 |
| JP | 7-128305 | 5/1995 |
| JP | 7-128314 | 5/1995 |
| JP | 9-304358 | 11/1997 |
| JP | 10-111282 | 4/1998 |
| JP | 2004-511774 | 4/2004 |
| JP | 3638814 | 4/2005 |
| JP | 2005-274557 | 10/2005 |
| JP | 2006-30218 | 2/2006 |
| JP | 2006-322900 | 11/2006 |
| JP | 2007-47116 | 2/2007 |
| JP | 2008-26061 | 2/2008 |

OTHER PUBLICATIONS

Office Action issued Jun. 20, 2013 in corresponding Chinese Patent Application No. 201080032305.0 (with English translation).
Japanese Decision to Grant Patent issued Oct. 22, 2013 in Japanese Patent Application No. 2009-191794.

* cited by examiner

ULTRASONIC TESTING PROBE AND ULTRASONIC TESTING APPARATUS

TECHNICAL FIELD

The present invention relates to an ultrasonic testing probe and an ultrasonic testing apparatus suitable for use particularly for a test of a butt-welded portion of a tube.

BACKGROUND ART

For a quality test of a butt-welded portion of a small-bore tube, such as a boiler tube, a radiation transmission test and an ultrasonic flaw-detection test are currently performed. In ultrasonic flaw detection, various flaw detection methods are used, such as an angle beam testing method for flaw detection using transverse ultrasonic waves and a creeping flaw-detection method using creeping waves (for example, see Patent Literatures 1 and 2).

In the radiation transmission test, another operation, such as a welding operation, cannot be performed at the same time because outsiders need to be evacuated from a controlled area during the test. Furthermore, because of a problem of workers' exposure to radiation, it is desirable to change the radiation transmission test to the ultrasonic flaw-detection test, if possible.

On the other hand, in the ultrasonic flaw-detection test, it is known that the above-described angle beam testing method for flaw detection has an advantage that, by making ultrasonic waves skip on the inner surface of the tube, the presence or absence of a flaw in the entire plate thickness of the tube can be detected with higher precision than in the creeping flaw-detection method.

On the other hand, in the creeping flaw-detection method, there is a known advantage that, since ultrasonic waves spread, the presence or absence of a flaw in the entire plate thickness of the tube can be detected in a shorter time than in the angle beam testing method for flaw detection.

Therefore, in some cases, a test for the presence or absence of a flaw is performed by using one or both of the angle beam testing method for flaw detection and the creeping flaw-detection method, depending on the object to be subjected to the ultrasonic flaw detection.

CITATION LIST

Patent Literature

{PTL 1}
Japanese Unexamined Patent Application, Publication No. 2006-030218
{PTL 2}
Japanese Unexamined Patent Application, Publication No. 2008-026061

SUMMARY OF INVENTION

Technical Problem

However, the above-described angle beam testing method for flaw detection has a problem in that, since ultrasonic waves are made to skip on the inner surface of the tube, the angle beam testing method for flaw detection can be used only for a smooth tube having a smooth inner surface, and a test for the presence or absence of a flaw by the angle beam testing method for flaw detection cannot be performed for a rifled tube having a helical groove formed therein. Furthermore, the angle beam testing method for flaw detection has a problem in that, since it is necessary to scan a pipe with a probe, the time required for a test for the presence or absence of a flaw is increased, compared with the creeping flaw-detection method.

On the other hand, the creeping flaw-detection method has a disadvantage that the flaw-detection capability is lower than that of the angle beam testing method for flaw detection. For example, there is a disadvantage that it is difficult to detect a blowhole having a diameter of about 1 mm.

Furthermore, when both the angle beam testing method and the creeping flaw-detection method are carried out, if a flaw is completely detected in both of a smooth tube and a rifled tube, for example, since the probe needs to be changed because different probes are used for the smooth tube and the rifled tube, there is a problem in that the time required for the flaw detection is increased.

The present invention has been made to solve the above-described problems, and an object thereof is to provide an ultrasonic testing probe and an ultrasonic testing apparatus capable of reducing the time required for flaw detection while maintaining the flaw-detection capability, irrespective of the shape of the inner surface of a tested object.

Solution to Problem

In order to achieve the above-described object, the present invention provides the following solutions.

According to a first aspect, the present invention provides an ultrasonic testing probe including: a first probe and a second probe, in each of which a plurality of oscillators that transmit ultrasonic waves to a tested object and detect ultrasonic waves reflected from the tested object are arrayed, in which the first probe is disposed closer to a flaw in the tested object than the second probe is, the first probe generates longitudinal ultrasonic waves that propagate on an inner surface of the tested object opposite to an outer surface thereof where the first probe and the second probe are disposed and transverse ultrasonic waves that propagate from the outer surface toward an inside of the tested object, and the second probe generates longitudinal ultrasonic waves that propagate on the outer surface and longitudinal ultrasonic waves that propagate from the outer surface toward the inside of the tested object.

According to the first aspect of the present invention, since the first probe generates longitudinal ultrasonic waves (secondary creeping waves) propagating on the inner surface, and the second probe detects the secondary creeping waves reflected at a flaw, a test for the presence or absence of a flaw (for example, incomplete penetration) on the inner surface can be performed irrespective of the shape of the inner surface. On the other hand, since the second probe generates longitudinal ultrasonic waves (creeping waves) propagating on the outer surface, and the first probe detects the creeping waves reflected at a flaw, a test for the presence or absence of a flaw (for example, lack of fusion) on the outer surface can be performed irrespective of the shape of the outer surface.

Furthermore, since a test for the presence or absence of a flaw is performed by using the creeping waves and the secondary creeping waves (by the creeping flaw-detection method), the time required for the flaw detection can be reduced compared with the angle beam testing method for flaw detection.

It is possible to generate, with the first probe, transverse ultrasonic waves propagating from the outer surface toward the inside of the tested object and to detect, with the second probe, the transverse ultrasonic waves reflected at a flaw; in other words, it is possible to perform a test for the presence or absence of a flaw by the transverse-wave angle beam testing method for flaw detection. Similarly, it is possible to generate, with the second probe, longitudinal ultrasonic waves propagating from the outer surface toward the inside of the tested object and to detect, with the first probe, the longitudinal ultrasonic waves reflected at a flaw; in other words, it is possible to perform a test for the presence or absence of a flaw by the longitudinal-wave angle beam testing method for flaw detection.

Furthermore, since the test for the presence or absence of a flaw is performed by the angle beam testing method for flaw detection, the test for the presence or absence of a flaw can be performed with higher precision than in the creeping flaw-detection method.

Furthermore, since the first probe and the second probe are provided, the ultrasonic testing probe of the present invention needs not be changed and can be used for a test for the presence or absence of a flaw performed by the angle beam testing method for flaw detection and the creeping flaw-detection method.

According to a second aspect, the present invention provides an ultrasonic testing apparatus including: an ultrasonic testing probe according to the above-described invention; a transmitting section that controls a transmission timing of ultrasonic waves from the plurality of oscillators of the first probe and the plurality of oscillators of the second probe; and a receiving section.

According to the second aspect of the present invention, the above-described ultrasonic testing probe of the present invention is provided, and the transmitting section controls the transmission timing of ultrasonic waves from the plurality of oscillators of the first probe and the plurality of oscillators of the second probe. Thus, it is possible to control generation of longitudinal ultrasonic waves propagating on the inner surface and generation of transverse ultrasonic waves propagating from the outer surface toward the inside of the tested object, in the first probe, and to control generation of longitudinal ultrasonic waves propagating on the outer surface and longitudinal ultrasonic waves propagating from the outer surface toward the inside of the tested object, in the second probe.

Advantageous Effects of Invention

According to the ultrasonic testing probe and the ultrasonic testing apparatus of the present invention, secondary creeping waves used for the creeping flaw-detection method are generated by the first probe, creeping waves are generated by the second probe, transverse ultrasonic waves used for the angle beam testing method for flaw detection are generated by the first probe, and longitudinal ultrasonic waves are generated by the second probe; thus, an advantage is afforded in that it is possible to reduce the time required for flaw detection while maintaining the flaw-detection capability, irrespective of the inner shape of a tested object.

DESCRIPTION OF EMBODIMENTS

An ultrasonic flaw-detecting apparatus according to one embodiment of the present invention will be described with reference to FIGS. 1 to 5.

Figure 1:
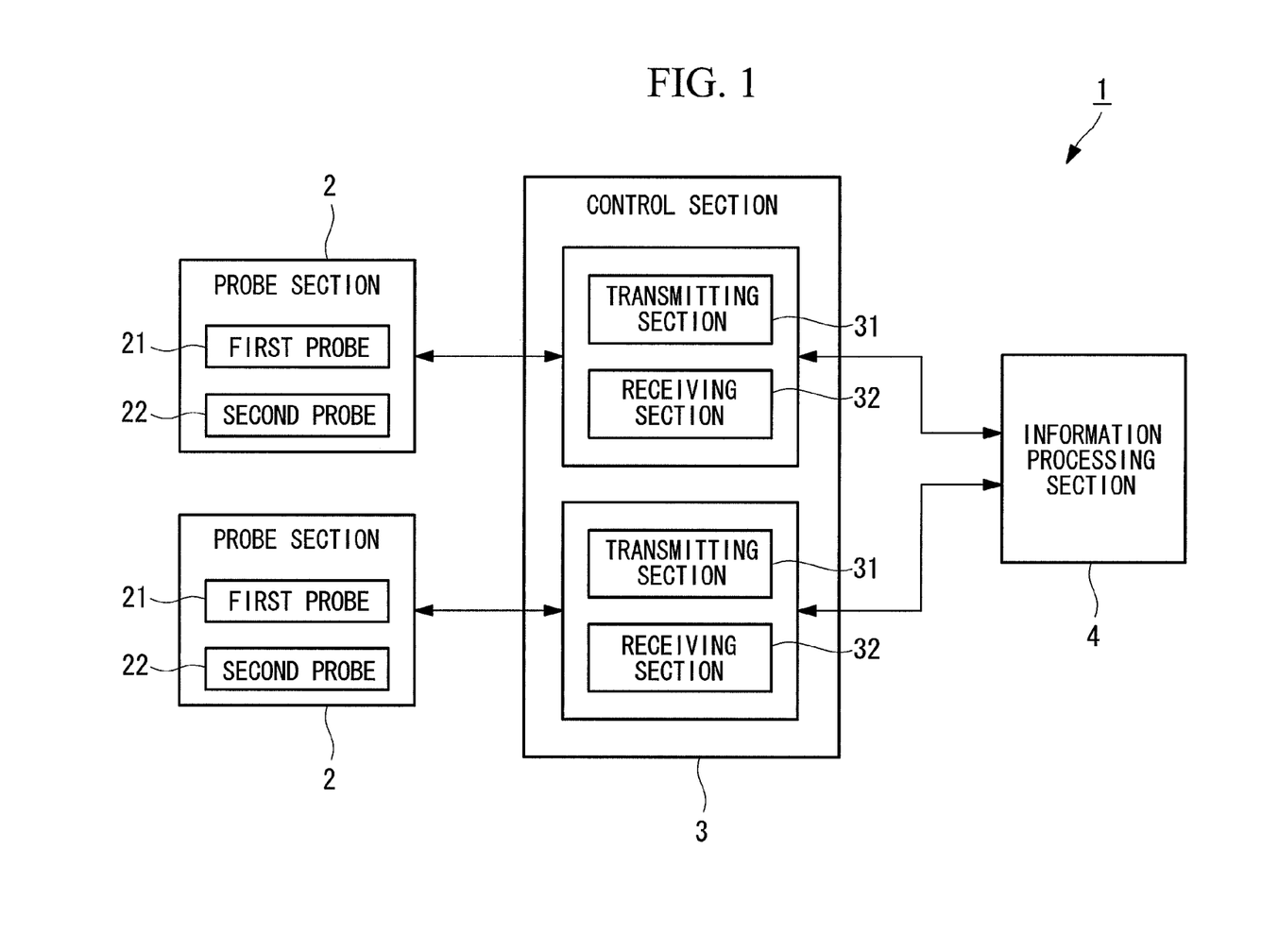
FIG. 1 is a schematic view for explaining, in outline, an ultrasonic flaw-detecting apparatus according to one embodiment of the present invention.
Figure 2:
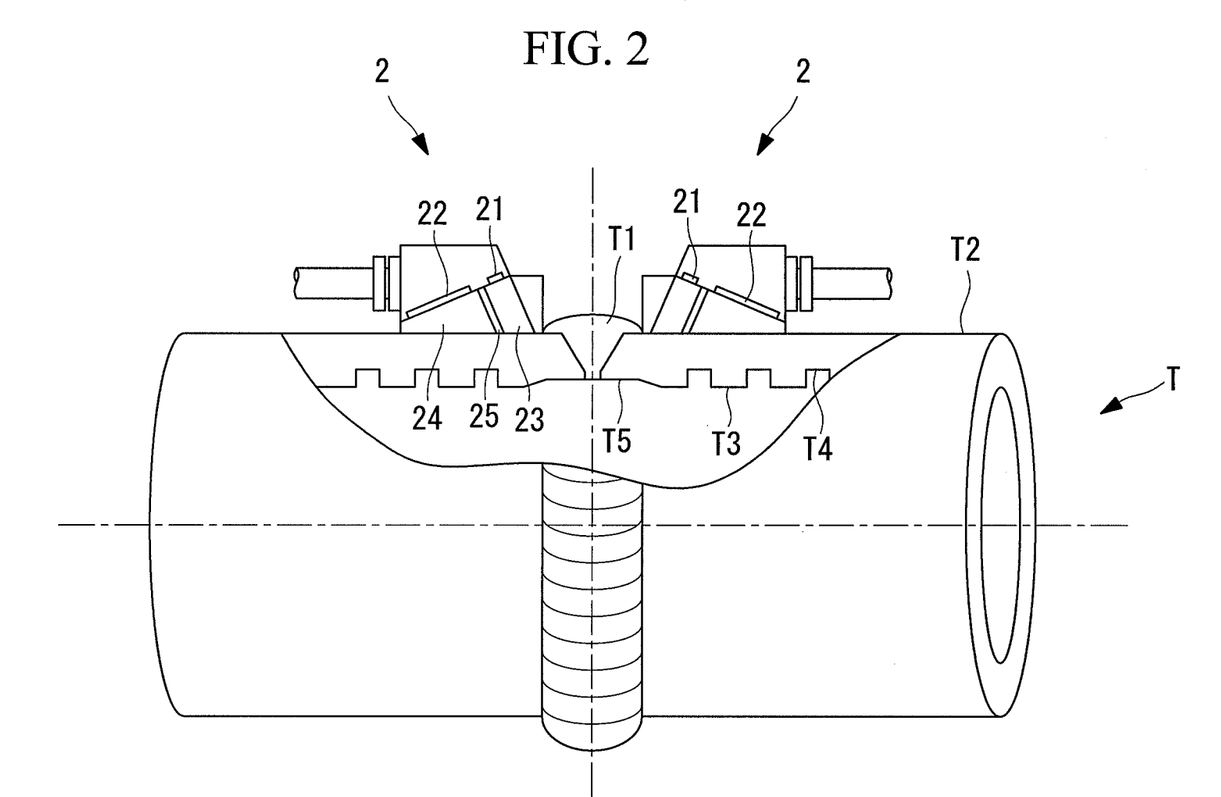
FIG. 2 is a schematic view for explaining a state in which probe sections shown in FIG. 1 are disposed on a boiler tube.

FIG. 1 is a schematic view for explaining, in outline, the ultrasonic flaw-detecting apparatus according to this embodiment. FIG. 2 is a schematic view for explaining a state in which probe sections shown in FIG. 1 are disposed on a boiler tube.

In this embodiment, a description is given of a case where the present invention is applied to an ultrasonic flaw-detecting apparatus 1 that detects the presence or absence of flaws, such as lack of fusion and incomplete penetration, in a butt-welded portion T1 of a boiler tube (tested object) T.

As shown in FIG. 1, the ultrasonic flaw-detecting apparatus 1 mainly includes a pair of probe sections (ultrasonic testing probes) 2, a control section 3, and an information processing section 4.

A description is given of a case where, as shown in FIG. 2, the boiler tube T used in this embodiment has an outer circumferential surface (outer surface) T2, rifling T4 formed on an inner circumferential surface T3, and a thinning portion (inner surface) T5 for adjusting the wall thickness of the boiler tube T, the thinning portion T5 being provided on the inner circumferential surface T3 in the vicinity of the butt-welded portion T1.

The surface of the thinning portion T5 is formed in a cylindrical shape unlike the inner circumferential surface T3.

As shown in FIG. 2, the probe sections 2 are disposed on the boiler tube T in the vicinity of the butt-welded portion T1, transmit ultrasonic waves toward the boiler tube T, and detect the ultrasonic waves reflected from the boiler tube T and the butt-welded portion T1.

Each of the probe sections 2 mainly includes a first probe 21, a second probe 22, a first wedge 23, and a second wedge 24. Ultrasonic waves generated from the first probe 21 and the second probe 22 enter the boiler tube T through the first wedge 23 and the second wedge 24, respectively.

The first probe 21 and the second probe 22 transmit ultrasonic waves and detect the ultrasonic waves reflected from a flaw and are used to detect flaws, such as lack of fusion and incomplete penetration, in the butt-welded portion T1 of the boiler tube T.

Furthermore, the first probe 21 and the second probe 22 are phased array probes in each of which a plurality of oscillators that transmit ultrasonic waves and detect ultrasonic waves are arrayed on surfaces thereof.

As shown in FIG. 2, the first probe 21 is disposed in the probe section 2 at a side close to a flaw in the boiler tube T (at a butt-welded portion T1 side) and is disposed facing the boiler tube T with the first wedge 23 disposed therebetween.

The second probe 22 is disposed in the probe section 2 at the side opposite to the side close to the flaw in the boiler tube T; in other words, the first probe 21 and the second probe 22 are disposed in that order in a direction away from the butt-welded portion T1. Furthermore, the second probe 22 is disposed facing the boiler tube T with the second wedge 24 disposed therebetween.

Hereinafter, in the probe section 2, the side where the first probe 21 is disposed is referred to as a front side, and the side where the second probe 22 is disposed is referred to as a rear side.

The first probe 21 and the second probe 22 are disposed so as to have inclinations approaching the boiler tube T from the front side toward the rear side. Furthermore, the oscillators of the first probe 21 and the oscillators of the second probe 22 are arrayed on circumferential surfaces having a central axis extending from the front side toward the rear side.

In this embodiment, a description is given of an example case where the oscillators of the first probe 21 and the oscillators of the second probe 22 are arrayed on the circumferential surfaces having a radius of about 50 mm.

A description is given of an example case where the number of oscillators (the number of elements) constituting the first probe 21 and the second probe 22 is about 8 to about 16, and the oscillator pitch (element pitch) is about 0.3 mm to about 0.6 mm.

For example, in the first probe 21, the oscillator pitch is the distance from the center of each of the plurality of oscillators constituting the first probe 21 in the direction of the central axis of the boiler tube to the center of an adjacent oscillator on the central axis of the boiler tube.

Furthermore, a description is given of an example case where, in the first probe 21, an angle between the normal with respect to the surface of the boiler tube T on which the probe section 2 is disposed and the normal with respect to the surface of the second probe 22 is about 28°. On the other hand, a description is given of an example case where, in the second probe 22, an angle between the normal with respect to the surface of the boiler tube T on which the probe section 2 is disposed and the normal with respect to the surface of the first probe 21 is about 28°.

The plurality of oscillators can be formed of a known piezoelectric material, for example, and the material thereof is not particularly limited.

Furthermore, the arrangement pattern of the plurality of probes can be appropriately selected from various arrangement patterns, depending on the shape of a tested object, such as the boiler tube T, and is not particularly limited.

The first wedge 23 and the second wedge 24 guide the ultrasonic waves transmitted from the first probe 21 and the second probe 22, respectively, to the boiler tube T and also guide the ultrasonic waves reflected from a flaw in the boiler tube T to the first probe 21 and the second probe 22.

A known material, such as plastic, can be used for the first wedge 23 and the second wedge 24, and the material thereof is not particularly limited.

The first wedge 23 is disposed between the first probe 21 and the boiler tube T.

In this embodiment, a description is given of an example case where an angle between the surface in contact with the first probe 21 and the surface in contact with the boiler tube T is about 28°.

The second wedge 24 is disposed between the second probe 22 and the boiler tube T.

In this embodiment, a description is given of an example case where an angle between the surface in contact with the second probe 22 and the surface in contact with the boiler tube T is about 23°.

Between the part formed of the first probe 21 and the first wedge 23 and the part formed of the second probe 22 and the second wedge 24, a sound absorbing portion 25 that absorbs ultrasonic waves is provided to prevent the ultrasonic waves from directly propagating therebetween. The sound absorbing portion 25 absorbs ultrasonic waves directly propagating therebetween, thereby suppressing generation of ultrasonic waves that hamper flaw detection, other than ultrasonic waves reflected from the boiler tube T and the butt-welded portion T1.

A known sound absorbing portion can be used as the sound absorbing portion 25, and the type thereof is not particularly limited.

The control section 3 controls ultrasonic waves transmitted from the probe sections 2 and transfers detection signals output from the probe sections 2 to the information processing section 4.

As shown in FIG. 1, the control section 3 mainly includes transmitting sections 31 and receiving sections 32.

Each of the transmitting sections 31 outputs, to the oscillators of the first probe 21 and the oscillators of the second probe 22, pulsed drive voltages for causing the oscillators to transmit ultrasonic waves. Furthermore, the transmitting section 31 controls the phases of the ultrasonic waves transmitted from the oscillators, thereby controlling the ultrasonic waves transmitted from the first probe 21 and the second probe 22.

In this embodiment, the transmitting section 31 outputs, to the oscillators of the first probe 21, drive voltages for causing the oscillators to transmit ultrasonic waves that generate secondary creeping waves on the inner circumferential surface T3 of the boiler tube T and ultrasonic waves that generate transverse ultrasonic waves propagating in the boiler tube T.

On the other hand, the transmitting section 31 outputs, to the oscillators of the second probe 22, drive voltages for causing the oscillators to transmit ultrasonic waves that generate creeping waves on the outer circumferential surface T2 of the boiler tube T and ultrasonic waves that generate longitudinal ultrasonic waves propagating in the boiler tube T.

A known transmitting section can be used as the transmitting section 31, and the type thereof is not particularly limited.

Each of the receiving sections 32 converts detection signals output from the oscillators of the first probe 21 and the oscillators of the second probe 22 into measurement signals that can be processed in the information processing section 4 and outputs the measurement signals to the information processing section 4. For example, the receiving section 32 converts the detection signals, which are analog signals, output from the oscillators of the first probe 21 and the second probe 22 into the measurement signals, which are digital signals that can be processed in the information processing section 4.

The receiving section 32 is connected to the oscillators of the first probe 21 and the oscillators of the second probe 22 so as to be able to receive the detection signals therefrom and is also connected to the information processing section 4 so as to be able to output the measurement signals thereto.

A known receiving section can be used as the receiving section 32, and the type thereof is not particularly limited.

The information processing section 4 calculates the position of a flaw in the butt-welded portion T1 of the boiler tube T based on the measurement signals received from the receiving section 32.

A known information processing section can be used as the information processing section 4, and the type thereof is not particularly limited.

Next, a test for the presence or absence of a flaw in the boiler tube T performed by using the thus-structured ultrasonic flaw-detecting apparatus 1 will be described.

In this embodiment, a description is given of an example case where, first, a test for the presence or absence of a flaw, specifically, a blowhole (BH), is performed by a transverse-wave angle beam testing method for flaw detection; second, a test for the presence or absence of lack of fusion (LF) on the outer circumferential surface T2 and incomplete penetration (IP) on the inner circumferential surface T3 is performed by a creeping flaw-detection method; and, finally, a test for the presence or absence of lack of fusion (LF) is performed by a longitudinal-wave angle beam testing method for a flaw detection.

Figure 3:
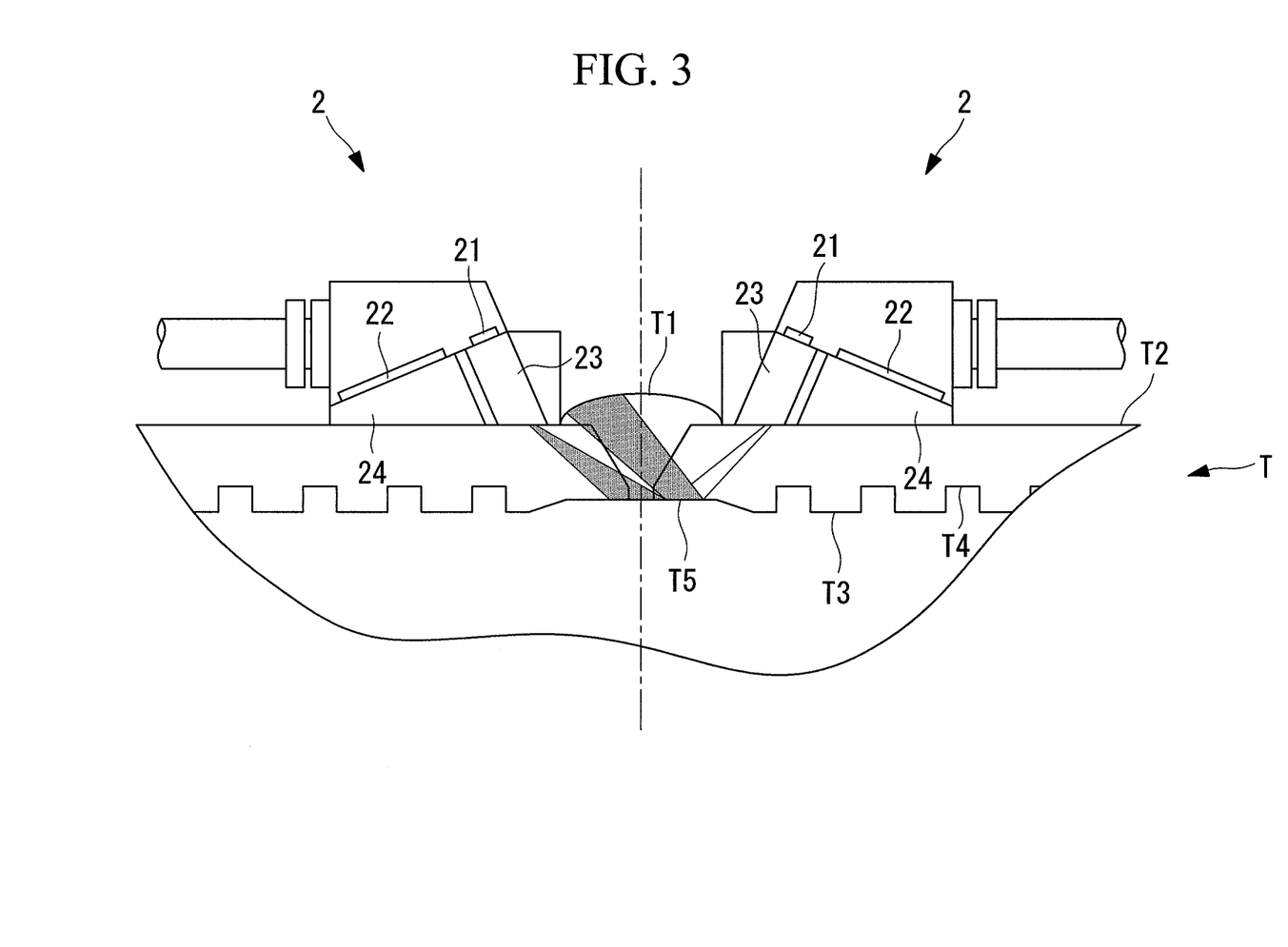
FIG. 3 is a schematic view for explaining a test for the presence or absence of a flaw performed by a transverse-wave angle beam testing method for flaw detection.

FIG. 3 is a schematic view for explaining a test for the presence or absence of a flaw performed by the transverse-wave angle beam testing method for flaw detection.

First, a test for the presence or absence of a flaw, such as a blowhole, performed by the transverse-wave angle beam testing method for flaw detection will be described.

As shown in FIG. 3, the probe sections 2 are disposed facing each other so as to sandwich the butt-welded portion T1 of the boiler tube T therebetween. At this time, the front sides, where the first probes 21 are disposed, are close to the butt-welded portion T1.

With ultrasonic waves transmitted from the first probes 21, transverse ultrasonic waves propagate in the boiler tube T. Each of the transmitting sections 31 controls the phases of the ultrasonic waves transmitted from the oscillators of the first probe 21, thereby controlling the direction of an ultrasonic beam transmitted from the first probe 21. Thus, the directions of the transverse ultrasonic waves propagating in the boiler tube T are controlled (sector-scanned).

Specifically, the ultrasonic waves transmitted from the first probe 21 propagate in the first wedge 23, enter the boiler tube T from the outer circumferential surface T2 of the boiler tube T, and propagate toward the inner circumferential surface T3 of the boiler tube T as transverse ultrasonic waves. The ultrasonic waves are refracted when entering the boiler tube T from the first wedge 23. In this embodiment, the transverse ultrasonic waves propagate within an angle range from about 38° to about 60° with respect to the direction of the normal of the outer circumferential surface T2.

The sector-scanned transverse ultrasonic waves directly enter the butt-welded portion T1 or enter the butt-welded portion T1 after being reflected at the thinning portion T5. In FIG. 3, transverse ultrasonic waves transmitted from the probe section 2 that is disposed at the left side directly enter the butt-welded portion T1, and transverse ultrasonic waves transmitted from the probe section 2 that is disposed at the right side are reflected at the thinning portion T5 to enter the butt-welded portion T1.

If a flaw, such as a blowhole, exists in the butt-welded portion T1, the transverse ultrasonic waves are reflected at the flaw.

The reflected ultrasonic waves propagate back to the outer circumferential surface T2 of the boiler tube T along the same path as that followed when they entered the boiler tube T. Then, the reflected ultrasonic waves enter the second wedge 24 from the outer circumferential surface T2, enter the second probe 22 from the second wedge 24, and are detected by the oscillators of the second probe 22.

The oscillators of the second probe 22 output detection signals corresponding to the intensities of the detected ultrasonic waves, and the detection signals are received by the receiving section 32, as shown in FIG. 1. The receiving section 32 converts the detection signals, which are analog signals, into measurement signals, which are digital signals, and outputs the measurement signals to the information processing section 4.

The information processing section 4 calculates the position of the flaw, such as a blowhole, based on the received measurement signals.

Figure 4:
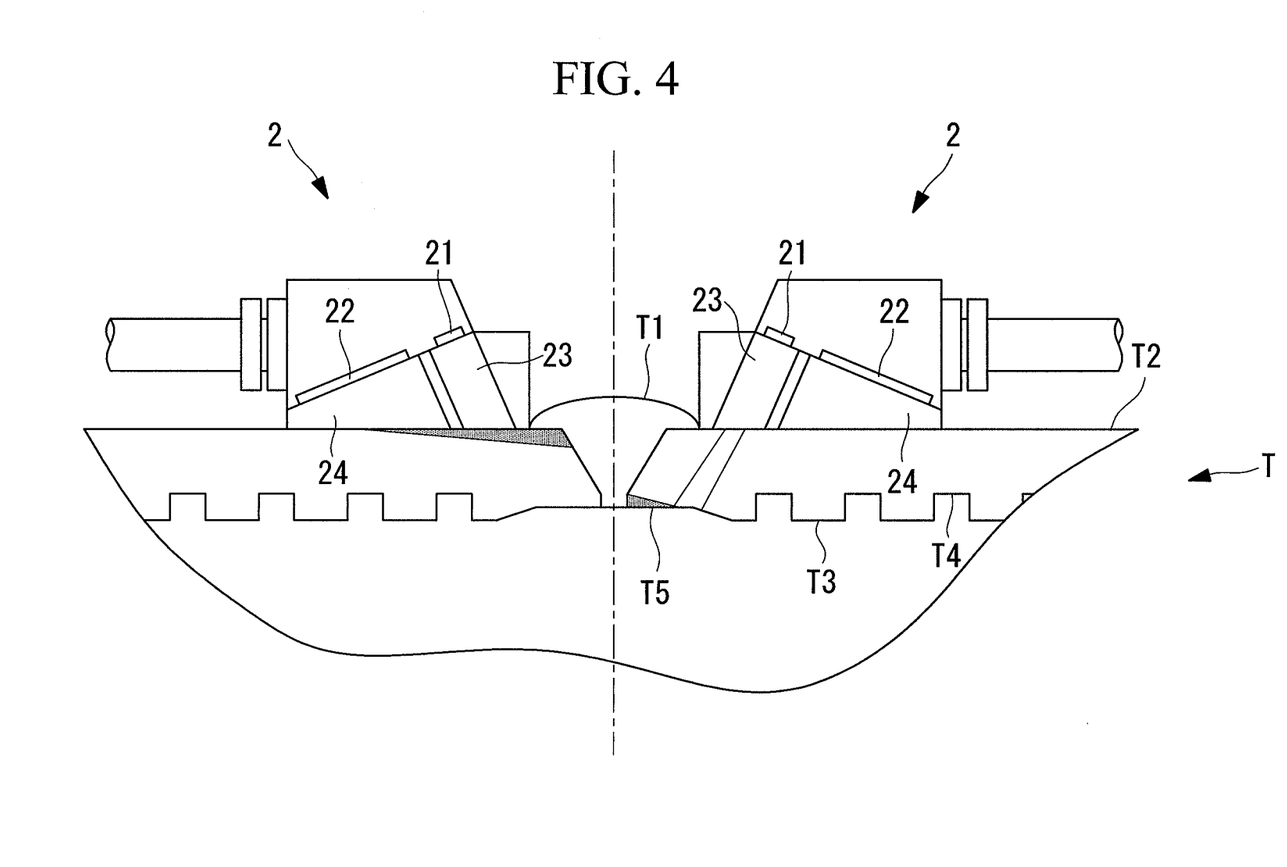
FIG. 4 is a schematic view for explaining a test for the presence or absence of a flaw performed by a creeping flaw-detection method.

FIG. 4 is a schematic view for explaining a test for the presence or absence of a flaw performed by the creeping flaw-detection method.

Next, a test for the presence or absence of a flaw, such as lack of fusion and incomplete penetration, performed by the creeping flaw-detection method will be described.

After the test for the presence or absence of a flaw by the transverse-wave angle beam testing method for flaw detection is completed, a test for the presence or absence of a flaw by the creeping flaw-detection method is performed next. Thus, a pair of the probe sections 2 is disposed at the same positions as in the test performed by the transverse-wave angle beam testing method for flaw detection.

First, a test for the presence or absence of a flaw, such as lack of fusion, performed by using creeping waves, which are ultrasonic waves propagating on the outer circumferential surface T2 of the boiler tube T, will be described with reference to the probe section 2 that is disposed at the left side in FIG. 4.

When the transmitting section 31 controls the phases of ultrasonic waves transmitted from the oscillators of the second probe 22, the ultrasonic waves transmitted from the second probe 22 are controlled, and longitudinal ultrasonic waves, that is, creeping waves, propagating along the outer circumferential surface T2 of the boiler tube T are generated.

Specifically, the ultrasonic waves transmitted from the second probe 22 propagate in the second wedge 24 and enter the outer circumferential surface T2 of the boiler tube T. Then, the creeping waves, which are longitudinal ultrasonic waves propagating along the outer circumferential surface T2, are generated.

The creeping waves propagate along the outer circumferential surface T2 and directly enter the butt-welded portion T1. If a flaw, such as lack of fusion, exists in the butt-welded portion T1, the creeping waves are reflected at the flaw. The reflected creeping waves enter the first wedge 23 from the boiler tube T along the same path as that followed when they entered the boiler tube T. The reflected creeping waves enter the first probe 21 from the first wedge 23 and are detected by the oscillators of the first probe 21.

The oscillators of the first probe 21 output detection signals corresponding to the intensities of the detected creeping waves. The subsequent operations are the same as those performed in the case of the test for the presence or absence of a flaw performed by the transverse-wave angle beam testing method for flaw detection, and therefore, a description thereof will be omitted.

Next, a test for the presence or absence of a flaw, such as incomplete penetration, performed by using secondary creeping waves, which are ultrasonic waves propagating on the inner circumferential surface T3 and the thinning portion T5 of the boiler tube T, will be described with reference to the probe section 2 that is disposed at the right side in FIG. 4.

When the transmitting section 31 controls the phases of ultrasonic waves transmitted from the oscillators of the first probe 21, the ultrasonic waves transmitted from the first probe 21 are controlled, and longitudinal ultrasonic waves, that is, secondary creeping waves, propagating along the thinning portion T5 of the boiler tube T are generated.

Specifically, the ultrasonic waves transmitted from the first probe 21 propagate in the first wedge 23 and enter the outer circumferential surface T2 of the boiler tube T, thus generating transverse ultrasonic waves propagating from the outer circumferential surface T2 toward the thinning portion T5. When the transverse ultrasonic waves enter the thinning portion T5, the secondary creeping waves, which are longitudinal ultrasonic waves propagating along the thinning portion T5, are generated.

The secondary creeping waves propagate along the thinning portion T5 and directly enter the butt-welded portion T1.

If a flaw, such as incomplete penetration, exists in the butt-welded portion T1, the secondary creeping waves are reflected at the flaw. The reflected secondary creeping waves enter the second wedge 24 from the boiler tube T along the same path as that followed when they entered the boiler tube T. The reflected secondary creeping waves enter the second probe 22 from the second wedge 24 and are detected by the oscillators of the second probe 22.

The oscillators of the second probe 22 output detection signals corresponding to the intensities of the detected secondary creeping waves. The subsequent operations are the same as those in the case of the test for the presence or absence of a flaw performed by the transverse-wave angle beam testing method for flaw detection, and therefore, a description thereof will be omitted.

Figure 5:
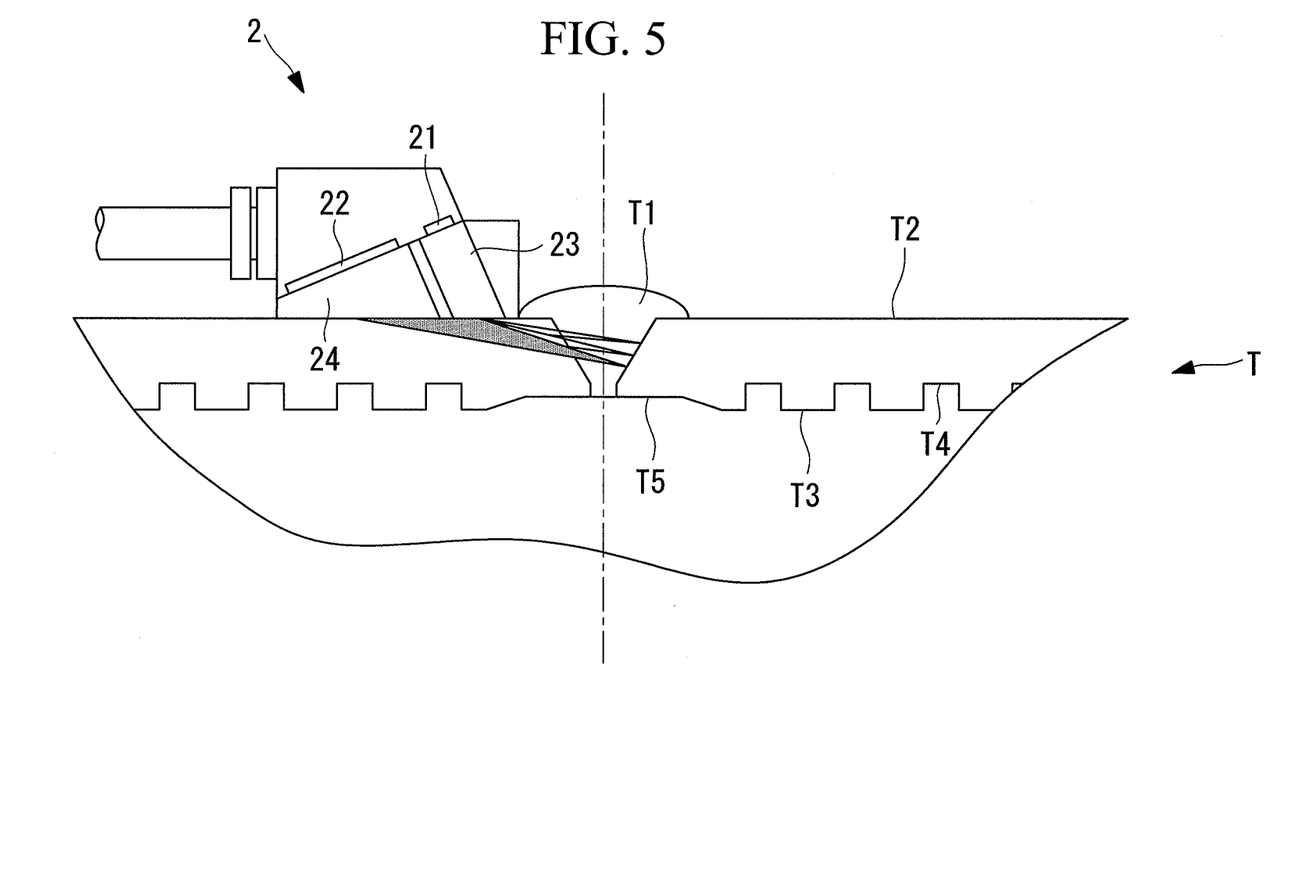
FIG. 5 is a schematic view for explaining a test for the presence or absence of a flaw performed by a longitudinal-wave angle beam testing method for flaw detection.

FIG. 5 is a schematic view for explaining a test for the presence or absence of a flaw performed by the longitudinal-wave angle beam testing method for flaw detection.

Finally, a test for the presence or absence of a flaw, such as lack of fusion, performed by the longitudinal-wave angle beam testing method for flaw detection will be described.

After the test for the presence or absence of a flaw by the creeping flaw-detection method is completed, a test for the presence or absence of a flaw by the longitudinal-wave angle beam testing method for flaw detection is performed next. Thus, a pair of the probe sections 2 is disposed at the same positions as in the tests performed by the transverse-wave angle beam testing method for flaw detection and the creeping flaw-detection method.

In FIG. 5, for ease of understanding, one of the probe sections 2 (the probe section 2 that is disposed at the left side) is shown.

When the transmitting section 31 controls the phases of ultrasonic waves transmitted from the oscillators of the second probe 22, ultrasonic waves transmitted from the second probe 22 are controlled, and longitudinal ultrasonic waves propagating from the outer circumferential surface T2 of the boiler tube T toward the inner circumferential surface T3 thereof are generated.

Specifically, the ultrasonic waves transmitted from the second probe 22 propagate in the second wedge 24, enter the boiler tube T from the outer circumferential surface T2 of the boiler tube T, and propagate toward the inner circumferential surface T3 of the boiler tube T as longitudinal ultrasonic waves. The ultrasonic waves are refracted when entering the boiler tube T from the second wedge 24. In this embodiment, the longitudinal ultrasonic waves propagate within an angle range from about 60° to about 80° with reference to the direction of the normal of the outer circumferential surface T2.

The longitudinal ultrasonic waves directly enter the butt-welded portion T1, and, if a flaw, such as lack of fusion, exists, they are reflected at the flaw.

The reflected ultrasonic waves propagate back to the outer circumferential surface T2 of the boiler tube T along the same path as that followed when they entered the boiler tube T. Then, the reflected ultrasonic waves enter the first wedge 23 from the outer circumferential surface T2, enter the first probe 21 from the first wedge 23, and are detected by the oscillators of the first probe 21.

The oscillators of the first probe 21 output detection signals corresponding to the intensities of the detected ultrasonic waves. The subsequent operations are the same as those in the case of the test for the presence or absence of a flaw performed by the transverse-wave angle beam testing method for flaw detection, and therefore, a description thereof will be omitted.

According to the above-described configuration, the first probe 21 generates secondary creeping waves, and the second probe 22 detects the secondary creeping waves reflected at a flaw; thus, it is possible to perform a test for the presence or absence of a flaw in the thinning portion T5 irrespective of the shape of the inner circumferential surface T3. On the other hand, the second probe 22 generates creeping waves, and the first probe 21 detects the creeping waves reflected at a flaw; it is possible to perform a test for the presence or absence of a flaw on the outer circumferential surface T2 irrespective of the shape of the outer circumferential surface T2.

Furthermore, since the test for the presence or absence of a flaw is performed by using the creeping waves and the secondary creeping waves, the time required for flaw detection can be reduced compared with the angle beam testing method for flaw detection.

It is possible to generate, with the first probe 21, transverse ultrasonic waves propagating from the outer circumferential surface T2 toward the inside of the boiler tube T and to detect, with the second probe 22, the transverse ultrasonic waves reflected at a flaw; that is, it is possible to perform a test for the presence or absence of a flaw by the transverse-wave angle beam testing method for flaw detection. Similarly, it is possible to generate, with the second probe 22, longitudinal ultrasonic waves propagating from the outer circumferential surface T2 toward the inside of the boiler tube T and to detect, with the first probe 21, the longitudinal ultrasonic waves reflected at a flaw; that is, it is possible to perform a test for the presence or absence of a flaw by the longitudinal-wave angle beam testing method for flaw detection.

Furthermore, since the test for the presence or absence of a flaw is performed by the angle beam testing method for flaw detection, the test for the presence or absence of a flaw can be performed with higher precision than in the creeping flaw-detection method.

Furthermore, since the first probe 21 and the second probe 22 are provided, the probe sections 2 and the ultrasonic flaw-detecting apparatus 1 of this embodiment can use them to detect the presence or absence of a flaw by the angle beam testing method for flaw detection and the creeping flaw-detection method, without changing the probe sections 2 themselves or the wedges.

REFERENCE SIGNS LIST 1 ultrasonic flaw-detecting apparatus
2 probe section (ultrasonic testing probe)
21 first probe
22 second probe
31 transmitting section
T boiler tube (tested object)
T2 outer circumferential surface (outer surface)
T5 thinning portion (inner surface)

The invention claimed is:

1. An ultrasonic testing probe comprising:
   a first probe and a second probe, in each of which a plurality of oscillators that transmit ultrasonic waves to a tested object and detect ultrasonic waves reflected from the tested object are arrayed,
   wherein the first probe is disposed closer to a flaw in the tested object than the second probe is,
   the first probe generates longitudinal first ultrasonic waves that propagate on an inner surface of the tested object opposite to an outer surface thereof where the first probe and the second probe are disposed and transverse second ultrasonic waves that propagate from the outer surface toward an inside of the tested object, the second probe generates longitudinal third ultrasonic waves that propagate on the outer surface and longitudinal fourth ultrasonic waves that propagate from the outer surface toward the inside of the tested object,
the first probe detects reflected waves of the longitudinal third ultrasonic waves and reflected waves of the longitudinal fourth ultrasonic waves, and
the second probe detects reflected waves of the longitudinal first ultrasonic waves and reflected waves of the transverse second ultrasonic waves.

2. An ultrasonic testing apparatus comprising:
an ultrasonic testing probe according to claim 1; and
a transmitting section that controls a transmission timing of ultrasonic waves from the plurality of oscillators of the first probe and the plurality of oscillators of the second probe.

* * * * *